(12) United States Patent
Yamaguchi et al.

(10) Patent No.: US 7,026,504 B2
(45) Date of Patent: Apr. 11, 2006

(54) PROCESS FOR PREPARING ALKYLADAMANTYL ESTERS AND COMPOSITIONS

(75) Inventors: Masao Yamaguchi, Shunan (JP); Hiromasa Yamamoto, Shunan (JP); Hideki Kikuchi, Shunan (JP); Yoshihiro Hirota, Shunan (JP)

(73) Assignee: Tokuyama Corporation, Shunan (JP)

( * ) Notice: Subject to any disclaimer, the term of this patent is extended or adjusted under 35 U.S.C. 154(b) by 405 days.

(21) Appl. No.: 10/470,126

(22) PCT Filed: Jan. 26, 2001

(86) PCT No.: PCT/JP01/00543

§ 371 (c)(1),
(2), (4) Date: Jul. 25, 2003

(87) PCT Pub. No.: WO02/059073

PCT Pub. Date: Aug. 1, 2002

(65) Prior Publication Data

US 2004/0077898 A1  Apr. 22, 2004

(51) Int. Cl.
*C07C 69/52* (2006.01)

(52) U.S. Cl. .................................................... 560/220

(58) Field of Classification Search .................... None
See application file for complete search history.

(56) References Cited

U.S. PATENT DOCUMENTS 6,239,231 B1 * 5/2001 Fujishima et al. .......... 525/337

FOREIGN PATENT DOCUMENTS

| JP | 5-265212 A | 10/1993 |
| JP | 8-310995 A | 11/1996 |
| JP | 10-182552 A | 7/1998 |
| JP | 2000-38362 A | 2/2000 |

* cited by examiner

*Primary Examiner*—Paul A. Zucker
(74) *Attorney, Agent, or Firm*—Birch, Stewart, Kolasch & Birch, LLP

(57) ABSTRACT

There is provided a method for obtaining a high-purity alkyladamantyl ester from an alkyladamantyl ester composition containing a large quantity of alkyladamantyl halide obtained by, for example, alkylating raw material 2-adamantanone obtained through oxidation of adamantane by use of an organic metal reagent and then causing an acid halide to react with the resulting product, efficiently by a simple process. To an alkyladamantyl ester composition containing an alkyladamantyl halide such as 2-chloro-2-methyladamantane in an amount of larger than 0.5 parts by weight based on 100 parts by weight of alkyladamantyl ester such as 2-methyl-2-adamantyl methacrylate, a mixed solution of, for example, methanol and a sodium hydroxide aqueous solution is added. By bringing the alkali compound into contact with the alkyladamantyl halide in a homogeneous system so as to convert the halide into a compound which produces no acid when heated, the amount of the alkyladamantyl halide in the composition is reduced to 0.5 parts by weight or less based on 100 parts by weight of the alkyladamantyl ester, after which distillation is carried out.

11 Claims, No Drawings

PROCESS FOR PREPARING ALKYLADAMANTYL ESTERS AND COMPOSITIONS

This application is the national phase under 35 U.S.C. § 371 of PCT International Application No. PCT/JP01/00543 which has an International filing date of Jan. 26, 2001, which designated the United States of America.

TECHNICAL FIELD

The present invention relates to a production method of an alkyladamantyl ester and a composition containing the alkyladamantyl ester. More specifically, the present invention relates to a production method of an alkyladamantyl ester which is useful as a raw material for a resist for a semiconductor and a composition containing the alkyladamantyl ester.

BACKGROUND ART

A resist obtained from an alkyladamantyl ester used as a raw material has been reported to have high dry etching resistance in a production process of a semiconductor (JP-A 5-265212), and the possibility of its use as a material for a resist for a semiconductor has been coming into notice.

In general, a compound used as a material for a resist for a semiconductor is required to be of high purity. Even in the case of the above alkyladamantyl ester, it is required to be of high purity when used as a material for a resist for a semiconductor. Particularly, the alkyladamantyl ester is stringently required to have a metal component reduced. Further, as a purification method capable of removing such a metal component efficiently, purification by distillation is suitable.

It is known that the alkyladamantyl ester is generally unstable with acids and is decomposed into an alkylidene adamantane and a carboxylic acid by a catalytic amount of acid. Therefore, it has been generally practiced that the alkyladamantyl ester is washed with an alkali aqueous solution such as a sodium hydroxide aqueous solution as a pretreatment when the alkyladamantyl ester is purified by distillation.

However, as a result of attempting to distill the alkyladamantyl ester by such a method, the present inventors have found that the alkyladamantyl ester decomposes easily during distillation depending on a synthesis method of the alkyladamantyl ester. That is, it has been found that an alkyladamantyl ester synthesized by alkylating 2-adamantanone with an organic metal reagent and then causing an acid halide to react with the resulting product decomposes during distillation and causes a blockage in a distillation device by sticking to the internal wall of the device, whereby purification by distillation may become substantially impossible.

The present inventors have made intensive studies so as to solve the above problem. As a result, they have found that an alkyladamantyl halide (hereinafter also referred to as "impurity halide") represented by the following formula (2):

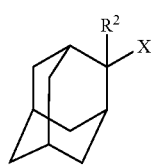

(wherein $R^2$ is an alkyl group having 1 to 6 carbon atoms, and X is a halogen atom)

is contained in an alkyladamantyl ester produced by such a method as described above, that the impurity halide is hardly removed by a conventional alkaline treatment using an alkaline aqueous solution in a heterogeneous system, that the impurity halide thermally decomposes at the time of distillation and produces a hydrogen halide which acts as a catalyst and decomposes a target alkyladamantyl ester. Under the circumstances, as a result of further studying a method of removing the impurity halide, the present inventors have found that although the impurity halide could not be removed efficiently and completely by a silica gel treatment or an activated carbon treatment, it can be removed efficiently by carrying out an alkaline treatment in a homogeneous system.

Further, the present inventors have also found in these studies that when the alkyladamantyl ester contains the above impurity halide in large quantity, there occur such problems that the alkyladamantyl ester decomposes and causes coloration and the like during storage or transportation and that a molecular weight does not increase at the time of polymerization.

DISCLOSURE OF THE INVENTION

An object of the present invention is to provide a method for obtaining a high-purity alkyladamantyl ester easily and efficiently from an alkyladamantyl ester synthesized by such a method as described above.

Another object of the present invention is to provide a method for producing a high-purity alkyladamantyl ester which is free from such problems as described above and has good storage stability in spite of containing a very small amount of impurity halide.

Still another object of the present invention is to provide an alkyladamantyl ester composition which has good storage stability in spite of containing a very small amount of impurity halide.

Other objects and advantages of the present invention will be apparent from the following description.

According to the present invention, firstly, the above objects and advantages of the present invention are achieved by a method for producing an alkyladamantyl ester, comprising the steps of:

bringing a raw material composition containing an alkyladamantyl halide represented by the following formula (2):

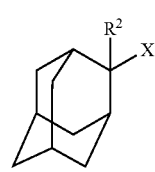

(wherein $R^2$ is an alkyl group having 1 to 6 carbon atoms, and X is a halogen atom)

in an amount of larger than 0.5 parts by weight based on 100 parts by weight of alkyladamantyl ester represented by the following formula (1):

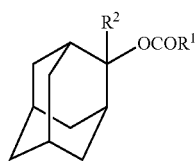

(wherein R¹ is an alkyl group having 1 to 6 carbon atoms or an alkenyl group having 2 to 6 carbon atoms, and R² is an alkyl group having 1 to 6 carbon atoms)
into contact with an alkali compound in the presence of an organic solvent which can dissolve the alkyladamantyl halide and the alkali compound to cause the alkyladamantyl halide and the alkali compound to react with each other, and subjecting the obtained mixture to distillation to obtain the alkyladamantyl ester.

According to the present invention, secondly, the above objects and advantages of the present invention are achieved by an alkyladamantyl ester composition which comprises 100 parts by weight of the alkyladamantyl ester represented by the above formula (1) and 0.01 to 0.5 parts by weight of the alkyladamantyl halide represented by the above formula (2).

The present inventors have confirmed that when the content of the impurity halide in the alkyladamantyl ester is higher than 0.5 parts by weight based on 100 parts by weight of the alkyladamantyl ester, the alkyladamantyl ester is decomposed by an acid produced by thermal decomposition of the impurity halide as described above. However, according to the above method of the present invention, the impurity halide is reacted with the alkali compound, whereby the impurity halide can be efficiently converted into a compound which produces no acid when heated, so that the content of the impurity halide can be reduced to such a level that does not cause a serious problem in distillation of the alkyladamantyl ester, more specifically, to 0.5 parts by weight or less based on 100 parts by weight of the alkyladamantyl ester.

Then, by distilling the raw material composition which has been brought into contact with the alkali compound as described above, decomposition of the target alkyladamantyl ester during distillation can be prevented effectively, and consequently, a high-purity alkyladamantyl ester can be obtained efficiently by a simple process, i.e., distillation of the above raw material composition.

Further, the alkyladamantyl ester composition of the present invention has a reduced content of the impurity halide of as low as 0.01 to 0.5 parts by weight based on 100 parts by weight of the alkyladamantyl ester. Therefore, even if the alkyladamantyl ester composition is distilled, decomposition of the alkyladamantyl ester does not occur during the distillation since the content of the impurity halide is small. Further, the above alkyladamantyl ester also has a characteristic that it has good storage stability. This composition can be obtained by, for example, bringing the above raw material composition into contact with an alkali compound in accordance with the above method.

PREFERRED EMBODIMENTS OF THE INVENTION

In the alkyladamantyl ester represented by the above formula (1), R¹ is an alkyl group having 1 to 6 carbon atoms or an alkenyl group having 2 to 6 carbon atoms. Illustrative examples of the alkyl group include straight-chain alkyl groups such as a methyl group, an ethyl group, a propyl group, a butyl group and a hexyl group; and branched-chain alkyl groups such as an isopropyl group, a tertiary butyl group and a neopentyl group. Meanwhile, illustrative examples of the alkenyl group include polymerizable groups such as a vinyl group and an isopropenyl group. R² is an alkyl group having 1 to 6 carbon atoms. Illustrative examples of the alkyl group include straight-chain alkyl groups such as a methyl group, an ethyl group, a propyl group, a butyl group and a hexyl group; and branched-chain alkyl groups such as an isopropyl group, a tertiary butyl group and a neopentyl group. Particularly, an alkyladamantyl ester represented by the above formula (1) wherein R¹ is a vinyl group or an isopropenyl group and R² is a methyl group, an ethyl group or a butyl group is suitable because the alkyladamantyl ester is useful as a raw material for a resist for a semiconductor and because a high degree of purification in particular is important.

In the impurity halide represented by the above formula (2), R² is an alkyl group having 1 to 6 carbon atoms which corresponds to R² in the above formula (1), and X is a halogen atom. Illustrative examples of the halogen atom include a chlorine atom, a bromine atom and an iodine atom. X is determined according to the types of organic metal reagent and acid halide used in a synthesis reaction to be described later of an alkyladamantyl ester. For example, when methylmagnesium bromide is used as the organic metal reagent and methacryloyl chloride is used as the acid halide, X is a bromine atom or a chlorine atom.

The mixing ratio of the alkyladamantyl ester and the impurity halide in a raw material composition is not particularly limited as long as the amount of the impurity halide is larger than 0.5 parts by weight based on 100 parts by weight of the alkyladamantyl ester. Such a raw material composition can be obtained by alkylating raw material 2-adamantanone obtained through oxidation of adamantane by use of an organic metal reagent and then causing an acid halide to react with the resulting product. In general, when an alkyladamantyl ester is produced by such a method, an impurity halide is by-produced, so that a raw material composition containing the impurity halide in an amount of about 0.7 to 5 parts by weight based on 100 parts by weight of the alkyladamantyl ester is obtained as a reaction mixed solution.

In the raw material composition, other impurity components may be contained in addition to the alkyladamantyl ester and the impurity halide as long as the other impurity components can be separated by distillation. Illustrative examples of such other impurity components include adamantane and 2-adamantanone which are used as raw materials at the time of synthesis of the alkyladamantyl ester, 1-adamantanol which is impurity contained in the raw material, 1-adamantyl ester and 2-alkylene adamantane which are by-produced at the time of synthesis, and tetrahydrofuran and hexane which are used as solvents at the time of synthesis.

The content of these other impurity components is not particularly limited. However, the total content of the other impurity components is generally about 1 to 30 parts by weight based on 100 parts by weight of the total weight of the alkyladamantyl ester and the impurity halide.

In the method of the present invention, the above raw material composition is brought into contact with an alkali compound before distillation of the raw material composition so as to cause the alkali compound to react with the impurity halide contained in the raw material composition (hereinafter also referred to as "alkaline treatment"). The reaction between the impurity halide and the alkali compound is a dehalogenation reaction. By this reaction, the impurity halide is converted into a compound which does not decompose and produce an acid when heated. The above dehalogenation reaction refers to a reaction in which halogen leaves the impurity halide and is a concept including a reaction in which introduction of a hydroxyl group or formation of an ether bond occurs along with elimination of halogen.

As the alkali compound, any alkali compound can be used without particular limitations as long as it shows alkalinity in the form of an aqueous solution. Illustrative examples of alkali compounds which may be suitably used in the present invention include alkali metal hydroxides such as sodium hydroxide and potassium hydroxide; alkali metal carbonates such as sodium carbonate; alkali metal bicarbonates such as potassium bicarbonate; quaternary ammonium hydroxides such as tetramethylammonium hydroxide and trimethylbenzylammonium hydroxide; organic amines such as triethylamine and pyridine; ammonia; alkali metal salts of organic acids such as sodium acetate and potassium benzoate; and metal alkoxides such as sodium methoxide and tertiary butoxy potassium. These are used alone or in combination.

The alkaline treatment is carried out in the presence of an organic solvent (hereinafter also referred to as "common solvent") which can dissolve the impurity halide and the alkali compound in the raw material composition. By doing so, the reaction between the impurity halide and the alkali compound can be carried out efficiently. At this time, they are preferably stirred so as to improve contact between them and may also be heated in some cases.

When the raw material composition is merely mixed with an alkali aqueous solution under agitation as described above, the reaction between the impurity halide and the alkali compound substantially does not occur, and even if they are stirred continuously for a long time, the amount of the impurity halide cannot be reduced to such a level that does not cause an adverse effect at the time of distillation.

As will be described later, the alkali compound may be used in the form of an aqueous solution, and in such a case as well, the reaction between the impurity halide and the alkali compound can be carried out in a good condition in the presence of a common solvent. At this time, the reaction system is preferably a homogeneous system. However, it goes without saying that an aqueous phase may be separated as long as the reaction proceeds to a sufficient extent and solids which are insoluble in the reaction solution may be precipitated during the reaction.

The common solvent used herein is not particularly limited as long as it is a solvent capable of dissolving both the impurity halide and the alkali compound. Specific examples of common solvents which can be suitably used include alcohols having 4 carbon atoms or less such as methanol, ethanol and isopropanol; glycols such as ethylene glycol, diethylene glycol and propylene glycol; water-soluble ethers such as tetrahydrofuran and dioxane; non-cyclic or cyclic aliphatic amides such as dimethylformamide and N-methylpyrrolidinone; sulfoxides and sulfolane such as dimethyl sulfoxide and sulfolane; and phosphoric amides such as hexamethyl phosphoric triamide. These common solvents can be used alone or as a mixed solvent.

Further, a mixed solvent of the above common solvent and water can be particularly suitably used from the viewpoint of solubility of the alkali compound. In this case, the amount of water is preferably 0.01 to 100 parts by weight, more preferably 0.1 to 50 parts by weight based on 100 parts by weight of the common solvent.

Conditions for the alkaline treatment can be selected as appropriate in consideration of the types of the raw material composition, alkali compound and solvent and other factors so that the amount of the impurity halide in the raw material composition can be reduced to such a level that can inhibit decomposition of the alkyladamantyl ester at the time of distillation. In general, the decomposition of the alkyladamantyl ester at the time of distillation depends on the amount of the coexisting impurity halide. The smaller the amount of the impurity halide, the less frequently the decomposition occurs. When an ordinary distillation device is used, the amount of the impurity halide is preferably smaller than 0.5 parts by weight, more preferably not larger than 0.2 parts by weight, particularly preferably not larger than 0.1 parts by weight, based on 100 parts by weight of the alkyladamantyl ester in order to inhibit decomposition of the alkyladamantyl ester at the time of distillation.

Suitable conditions for the alkaline treatment are as follows. The concentration of the alkali compound is sufficiently at least 1 mole per mole of the impurity halide contained in the raw material composition and can be generally selected from 1 to 100 moles, suitably 1.1 to 10 moles. The amount of the common solvent is sufficiently an amount which can dissolve the impurity halide and the alkali compound in the raw material composition completely. It can be generally 1 to 10,000 parts by weight, suitably 10 to 1,000 parts by weight, based on 1 part by weight of the total amount of the impurity halide and the alkali compound. Further, the treatment temperature may be any temperature ranging from room temperature to the boiling point of a solvent to be used according to the types of the common solvent and alkali compound to be used. The treatment temperature generally ranges from room temperature to 150° C., more preferably room temperature to 100° C. When the composition is heated at the time of the treatment, it is preferable to make sure in advance that the target alkyladamantyl ester is stable at a temperature at which the composition is heated.

The amount of the impurity halide after the alkaline treatment can be checked by analyzing the treated solution by gas chromatography.

By the above method, a mixture containing the impurity halide in an amount of smaller than 0.5 parts by weight based on 100 parts by weight of the alkyladamantyl ester can be obtained. This composition is obtained for the first time by the present invention. The content of the impurity halide in the above composition can be 0.01 to 0.5 parts by weight, more suitably 0.01 to 0.2 parts by weight, according to the above method.

The composition having a reduced content of the impurity halide has such characteristics that the alkyladamantyl ester hardly decomposes when the composition is stored under general conditions over an extended time period and that it has high storage stability. Such characteristics are not affected by the presence of impurities other than the impurity halide which may be generally contained, and similar effects are attained for the composition immediately after the-alkaline treatment and for the composition after distillation.

In the present invention, a high-purity alkyladamantyl ester can be obtained by subjecting the composition obtained by the above alkaline treatment to distillation.

The composition after the alkaline treatment may be distilled as it is. However, to attain high distillation efficiency, the above composition is desirably subjected to a post-treatment according to the common solvent used in the alkaline treatment before distillation is carried out. More specifically, when the common solvent can be easily distilled off under a reduced pressure, it is preferable that the common solvent be distilled off under a reduced pressure, another water-insoluble solvent which dissolves the alkyladamantyl ester be added, the resulting mixture be washed with water, an organic layer be dried and the solvent added be distilled off under a reduced pressure. Meanwhile, when the common solvent cannot be easily distilled off under a reduced pressure, the step of distilling of f the common solvent under a reduced pressure may be omitted.

A distillation method is not particularly limited. A known distillation method such as simple distillation, fractional distillation, Kugel roll or thin-film distillation can be employed. For example, in the case of the fractional distillation, a thin-film-type fractionating column such as a vigoureux-type column, a concentric tube column, a spinning band column or a packed column or a plate-type fractionating column such as a bubble-cap tower or a perforated-plate column is suitably used as a fractionating column. When reduced-pressure distillation is carried out, a thin-film-type fractionating column with a low pressure loss is particularly suitably used. Further, distillation conditions including a temperature, a pressure and a reflux ratio are also not particularly limited and can be determined as appropriate according to the composing of a composition to be purified, the type and amount of distillation assistant, the purity of a target compound which is eventually obtained and other factors.

EXAMPLES

Hereinafter, the present invention will be described in detail with reference to Examples. However, the present invention shall not be limited by these Examples in any way.

Example 1

To 1 part by weight of crude 2-methyl-2-adamantyl methacrylate (purity: 78.8 wt %) containing 1.9 wt % of 2-chloro-2-methyladamantane as an impurity, 5 parts by weight of methanol and 0.1 parts by weight (2.4 moles per mole of 2-chloro-2-methyladamantane) of 10% sodium hydroxide aqueous solution were added, and the mixture was refluxed for 3 hours. After it was confirmed by a gas chromatograph that 2-chloro-2-methyladamantane disappeared, methanol was distilled off under a reduced pressure. Thereafter, 5 parts by weight of hexane was added, the mixture was washed with 1 part by weight of water, the hexane layer was dried over magnesium sulfate, and hexane was then distilled off under a reduced pressure. As a result of analyzing the content of 2-chloro-2-methyladamantane in the composition by a gas chromatograph after removal of methanol, it was 0.06 parts by weight based on 100 parts by weight of 2-methyl-2-adamantyl methacrylate.

To 1 part by weight of crude 2-methyl-2-adamantyl methacrylate after removal of hexane, 0.1 parts by weight of diethylene glycol was added, and a 5-cm vigoureux-type fractionating column and a whole-condensation-type reflux fractionating device were used to distill crude 2-methyl-2-adamantyl methacrylate under a reduced pressure of 0.3 mmHg with air introduced by means of a glass capillary. Although 2-adamantanone and 2-methyl-2-adamantanol contained as impurities initially sublimed and stuck to the wall of the distillation device, they were dissolved by diethylene glycol which was subsequently distilled out and thereby come off the wall, whereby they could be fractionated. Then, 2-methyl-2-adamantyl methacrylate which was subsequently distilled out was collected. Thereby, 2-methyl-2-adamantyl methacrylate with a purity of 97 wt % could be obtained without being decomposed.

Example 2

To 1 part by weight of crude 2-methyl-2-adamantyl methacrylate (purity: 78.8 wt %) used in Example 1, 5 parts by weight of ethanol and 0.1 parts by weight (1.2 moles per mole of 2-chloro-2-methyladamantane) of 5% sodium hydroxide aqueous solution were added, and the mixture was then refluxed under heating. After it was confirmed by a gas chromatograph that the strength of 2-chloro-2-methyladamantane decreased by a factor of at least 4, ethanol was distilled off under a reduced pressure. Thereafter, 5 parts by weight of hexane was added, the mixture was washed with 1 part by weight of water, the hexane layer was dried over magnesium sulfate, and hexane was then distilled off under a reduced pressure. As a result of analyzing the content of 2-chloro-2-methyladamantane in the composition by a gas chromatograph after removal of ethanol, it was 0.43 parts by weight based on 100 parts by weight of 2-methyl-2-adamantyl methacrylate.

Diethylene glycol was added to crude 2-methyl-2-adamantyl methacrylate after removal of hexane in the same manner as in Example 1 so as to distill it, whereby 2-methyl-2-adamantyl methacrylate having a purity of 94 wt % could be obtained.

Example 3

To 1 part by weight of crude 2-ethyl-2-adamantyl methacrylate (purity: 86 wt %) containing 0.8 wt % of 2-chloro-2-ethyladamantane as an impurity, 5 parts by weight of methanol and 0.1 parts by weight (6.2 moles per mole of 2-chloro-2-ethyladamantane) of 10% sodium hydroxide aqueous solution were added, and the mixture was refluxed for 3 hours. After it was confirmed by a gas chromatograph that 2-chloro-2-ethyladamantane disappeared, methanol was distilled off under a reduced pressure. Thereafter, 5 parts by weight of hexane was added, the mixture was washed with 1 part by weight of water, the hexane layer was dried over magnesium sulfate, and hexane was then distilled off under a reduced pressure. As a result of analyzing the content of 2-chloro-2-ethyladamantane in the composition after removal of methanol by a gas chromatograph, it was 0.03 parts by weight based on 100 parts by weight of 2-ethyl-2-adamantyl methacrylate.

To 1 part by weight of crude 2-ethyl-2-adamantyl methacrylate after removal of hexane, 0.1 parts by weight of diethylene glycol and 0.1 parts by weight of tetraethylene glycol were added, and a 5-cm vigoureux-type fractionating column and a whole-condensation-type reflux fractionating device were used to distill crude 2-ethyl-2-adamantyl methacrylate under a reduced pressure of 0.3 mmHg with air introduced by means of a glass capillary. Although 2-adamantanone and 2-ethyl-2-adamantanol contained as impurities initially sublimed and stuck to the wall of the distillation device, they were dissolved by diethylene glycol and tetraethylene glycol which were subsequently distilled out and thereby come off the wall, whereby they could be fractionated. Then, 2-ethyl-2-adamantyl methacrylate which was subsequently distilled out was collected. Thereby, 2-ethyl-2-adamantyl methacrylate with a purity of 96 wt % could be obtained without being decomposed. This 2-ethyl-2-adamantyl methacrylate became solid at room temperature.

Example 4

To 1 part by weight of crude 2-butyl-2-adamantyl methacrylate (purity: 82 wt %) containing 1.2 wt % of 2-chloro-2-butyladamantane as an impurity, 5 parts by weight of methanol and 0.1 parts by weight (4.7 moles per mole of 2-chloro-2-butyladamantane) of 10% sodium hydroxide aqueous solution were added, and the mixture was refluxed for 3 hours. After it was confirmed by a gas chromatograph that 2-chloro-2-butyladamantane disappeared, methanol was distilled off under a reduced pressure. Thereafter, 5 parts by weight of hexane was added, the mixture was washed with 1 part by weight of water, the hexane layer was dried over magnesium sulfate, and hexane was then distilled off under a reduced pressure. As a result of analyzing the content of 2-chloro-2-butyladamantane in the composition after removal of methanol by a gas chromatograph, it was 0.04 parts by weight based on 100 parts by weight of 2-butyl-2-adamantyl methacrylate.

To 1 part by weight of crude 2-butyl-2-adamantyl methacrylate after removal of hexane, 0.1 parts by weight of tetraethylene glycol was added, and a 5-cm vigoureux-type fractionating column and a whole-condensation-type reflux fractionating device were used to distill crude 2-butyl-2-adamantyl methacrylate under a reduced pressure of 0.3 mmHg with air introduced by means of a glass capillary. Although 2-adamantanone and 2-butyl-2-adamantanol contained as impurities initially sublimed and stuck to the wall of the distillation device, they were dissolved by diethylene glycol which was subsequently distilled out and thereby come off the wall, whereby they could be fractionated. Then, 2-butyl-2-adamantyl methacrylate which was subsequently distilled out was collected. Thereby, 2-butyl-2-adamantyl methacrylate with a purity of 97 wt % could be obtained without being decomposed.

Comparative Example 1

The same crude 2-methyl-2-adamantyl methacrylate as used in Example 1 was directly distilled under a reduced pressure under the same conditions as used in Example 1. As a result, methacrylic acid and 2-methylene adamantane were mainly distilled out. Further, 2-methylene adamantane stuck to the internal wall of the distillation device and caused a blockage. Thus, crude 2-methyl-2-adamantyl methacrylate could not be purified by distillation.

Example 5

To 2-methyl-2-adamantyl methacrylate with a purity of 97% which contained substantially no 2-chloro-2-methyladamantane and was obtained in Example 1, separately produced 2-chloro-2-methyladamantane was added in amounts of 0.03 parts by weight, 0.48 parts by weight, 3.1 parts by weight and 6.3 parts by weight based on 100 parts by weight of 2-methyl-2-adamantyl methacrylate, thereby preparing 2-methyl-2-adamantyl methacrylate compositions. The storage stabilities of the compositions were examined at 50° C. As a result, while no coloration was observed in the compositions containing 0.01 parts by weight and 0.48 parts by weight of 2-chloro-2-methyladamantane after 2 months, slight coloration was observed in the composition containing 3.1 parts by weight of 2-chloro-2-methyladamantane, and the composition containing 6.3 parts by weight of 2-chloro-2-methyladamantane turned into a dark brown liquid.

EFFECTS OF THE INVENTION

According to the production method of the present invention, a purified alkyladamantyl ester can be easily obtained from a crude alkyladamantyl ester (raw material composition) containing a halide as an impurity by a simple process such as distillation. When a method which inevitably undergoes by-production of an alkyladamantyl halide is used in production of an alkyladamantyl ester, the production method of the present invention is extremely useful as a method for producing a high-purity alkyladamantyl ester.

Further, an alkyladamantyl ester in the composition of the present invention which is obtained by subjecting the raw material composition to an alkaline treatment is not decomposed even when heated, such that it can be subjected to such a treatment as distillation as it is and also be stored stably for a long time.

The invention claimed is:

1. A method for producing an alkyladamantyl ester, comprising the steps of: bringing a raw material composition containing an alkyladamantyl halide represented by the following formula (2):

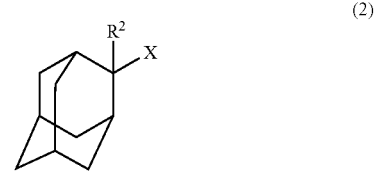

(wherein $R^2$ is an alkyl group having 1 to 6 carbon atoms, and X is a halogen atom)

in an amount of larger than 0.5 parts by weight based on 100 parts by weight of alkyladamantyl ester represented by the following formula (1):

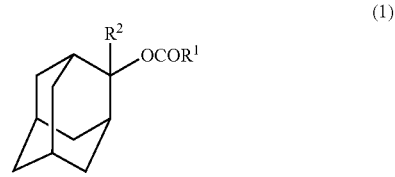

(wherein $R^1$ is an alkyl group having 1 to 6 carbon atoms or an alkenyl group having 2 to 6 carbon atoms, and $R^2$ is an alkyl group having 1 to 6 carbon atoms)

into contact with an alkali compound in the presence of an organic solvent which can dissolve the alkyladamantyl halide and the alkali compound to cause the alkyladamantyl halide and the alkali compound to react with each other, and subjecting the obtained mixture to distillation to obtain the alkyladamantyl ester.

2. The method of claim 1, wherein after the reaction, the alkyladamantyl halide remains in an amount of not larger than 0.5 parts by weight based on 100 parts by weight of the alkyladamantyl ester.

3. The method of claim 1, wherein the alkali compound is a compound which shows alkalinity in the form of an aqueous solution.

4. The method of claim 1, wherein the alkali compound is an alkali metal hydroxide, an alkali metal carbonate, an alkali metal bicarbonate, a quaternary ammonium hydroxide, an organic amine, ammonia, an alkali metal salt of an organic acid or a metal alkoxide.

5. The method of claim 1, wherein the alkali compound is used in an amount of 1 to 100 moles per mole of the alkyladamantyl halide.

6. The method of claim 1, wherein the organic solvent is an alcohol having 4 carbon atoms or less, a glycol, a water-soluble ether, a non-cyclic or cyclic aliphatic amide, a sulfoxide, a sulfolane or a phosphoric amide.

7. The method of claim 1, wherein the organic solvent is used in such an amount that can dissolve both the alkyladamantyl halide and the alkali compound which exist in the reaction system.

8. The method of claim 1, wherein the organic solvent is used in an amount of 10 to 1,000 parts by weight based on 1 part by weight of the total of the alkyladamantyl halide and the alkali compound.

9. The method of claim 1, wherein the organic solvent is used as a mixed solvent with water.

10. The method of claim 9, wherein the mixed solvent contains water in an amount of 0.01 to 100 parts by weight based on 100 parts by weight of the organic solvent.

11. An alkyladamantyl ester composition comprising 100 parts by weight of alkyladamantyl ester represented by the following formula (1):

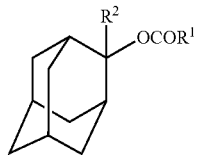

(1)

(wherein $R^1$ is an alkyl group having 1 to 6 carbon atoms or an alkenyl group having 2 to 6 carbon atoms, and $R^2$ is an alkyl group having 1 to 6 carbon atoms)

and 0.01 to 0.5 parts by weight of alkyladamantyl halide represented by the following formula (2):

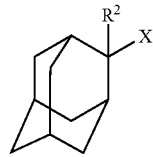

(2)

(wherein $R^2$ is an alkyl group having 1 to 6 carbon atoms, and X is a halogen atom).

* * * * *